US011304847B2

(12) United States Patent
Weinstein

(10) Patent No.: US 11,304,847 B2
(45) Date of Patent: Apr. 19, 2022

(54) THERMAL PACK THAT APPROXIMATES A CURVED THREE-DIMENSIONAL SURFACE

(71) Applicant: Randy Howard Weinstein, Windsor, CA (US)

(72) Inventor: Randy Howard Weinstein, Windsor, CA (US)

(*) Notice: Subject to any disclaimer, the term of this patent is extended or adjusted under 35 U.S.C. 154(b) by 51 days.

(21) Appl. No.: 15/940,861

(22) Filed: Mar. 29, 2018

(65) Prior Publication Data

US 2019/0380866 A1 Dec. 19, 2019

Related U.S. Application Data

(63) Continuation-in-part of application No. 15/553,988, filed as application No. PCT/US2017/024871 on Mar. 29, 2017.

(51) Int. Cl.
*A61F 7/10* (2006.01)
*A61F 7/02* (2006.01)
*A61F 7/08* (2006.01)
*A61F 7/00* (2006.01)

(52) U.S. Cl.
CPC ............ *A61F 7/10* (2013.01); *A61F 7/02* (2013.01); *A61F 7/08* (2013.01); *A61F 2007/0098* (2013.01); *A61F 2007/108* (2013.01)

(58) Field of Classification Search
CPC ...... A61F 2007/0098; A61F 7/10; A61F 7/02; A61F 7/08; A61F 2007/108; A61F 7/03; B65B 9/08
See application file for complete search history.

(56) References Cited

U.S. PATENT DOCUMENTS

| 2,337,550 A | 12/1943 | Crosby ................... 264/250 |
| 3,830,676 A | 8/1974 | Elkins |
| 5,107,444 A | 4/1992 | Wu |
| 5,230,335 A | 7/1993 | Johnson, Jr. et al. ...... 128/400 |
| 5,423,875 A * | 6/1995 | Kehe ................... A61F 7/10 607/112 |
| 5,496,357 A | 3/1996 | Jensen et al. |
| 5,634,940 A | 6/1997 | Panyard |
| 5,683,439 A | 11/1997 | Jensen |

(Continued)

FOREIGN PATENT DOCUMENTS

| CN | 106166097 | 11/2016 | |
| EP | 2208484 | 7/2010 | ............... A61F 7/10 |

(Continued)

OTHER PUBLICATIONS

International Search Report and Written Opinion issued in corresponding foreign application, PCT/US2017/024871, pp. 1-6 (dated May 22, 2017).

(Continued)

*Primary Examiner* — Kaitlyn E Smith
*Assistant Examiner* — Sean W Collins
(74) *Attorney, Agent, or Firm* — Benjamin D. Rotman; Golan Christie Taglia LLP

(57) ABSTRACT

A thermal pack comprising one or more sacks, a body of thermal material enclosed in the sacks, and first and a second sack edge joined to form a seam line wherein the first edge and the second edge have intersecting directions with an angle that is less than 180 degrees whereby the one or more sacks conforms to a three-dimensional surface.

20 Claims, 4 Drawing Sheets

(56) References Cited

U.S. PATENT DOCUMENTS

| | | | |
|---|---|---|---|
| 9,439,803 B2 | 9/2016 | Varga et al. | A61F 7/02 |
| 2003/0204227 A1 | 10/2003 | Ingram et al. | 607/114 |
| 2004/0064168 A1 | 4/2004 | Eischen | |
| 2008/0150191 A1* | 6/2008 | Giloh | B44C 3/046 |
| | | | 264/299 |
| 2008/0288033 A1 | 11/2008 | Mason et al. | 607/96 |
| 2010/0057173 A1 | 3/2010 | Leavitt | |
| 2012/0316626 A1 | 12/2012 | Dolivier et al. | 607/108 |
| 2013/0116760 A1 | 5/2013 | Carson et al. | A61F 7/10 |
| 2014/0107739 A1* | 4/2014 | Kirkman | A61F 7/103 |
| | | | 607/112 |
| 2014/0277301 A1 | 9/2014 | Varga | |
| 2014/0311100 A1* | 10/2014 | Tilley | B29C 66/81417 |
| | | | 53/479 |
| 2014/0360030 A1* | 12/2014 | Grove | A41H 3/04 |
| | | | 33/17 R |
| 2015/0224015 A1* | 8/2015 | Wilford | A61F 7/02 |
| | | | 601/151 |
| 2016/0051404 A1 | 2/2016 | Choucair et al. | A61F 7/10 |

FOREIGN PATENT DOCUMENTS

| | | | |
|---|---|---|---|
| JP | H06178792 | 8/1994 | |
| JP | 2000217685 A | 8/2000 | |
| KR | 20040019830 | 3/2004 | A61F 7/02 |
| KR | 20130044897 | 3/2013 | |
| WO | 2015-0120368 | 8/2015 | A61H 39/06 |

OTHER PUBLICATIONS

International Search Report and Written Opinion issued in corresponding foreign application, PCT/US2018/025287, pp. 1-11 (dated Sep. 25, 2018).

Second Office Action issued in corresponding foreign application, CN201880000941.1, pp. 1-11 (dated May 8, 2020).

Extended European Search Report issued in corresponding foreign application, EP 17856940.6, pp. 1-7 (dated Apr. 21, 2020).

First Office Action issued in corresponding foreign application, CN201880000941.1, pp. 1-10, (dated Dec. 2, 2019).

Extended European Search Report issued in corresponding foreign application, EP 18778334.5, pp. 1-7 (dated Dec. 18, 2020).

Office action Issued by the JPO for application 2019-517240.

Third Office Action issued in corresponding foreign application, CN201880000941.1, pp. 1-9 (dated Sep. 10, 2020).

\* cited by examiner

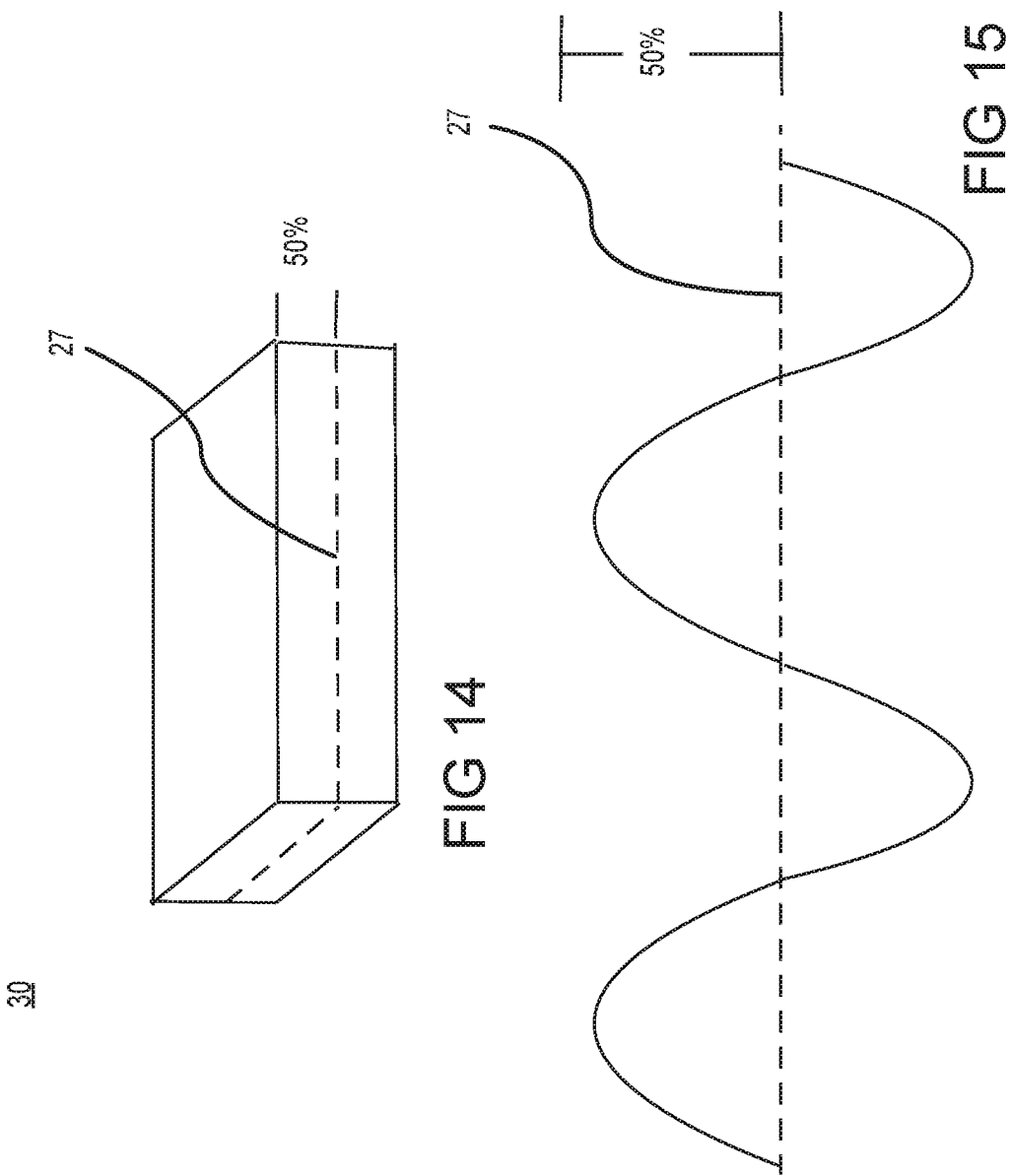

THERMAL PACK THAT APPROXIMATES A CURVED THREE-DIMENSIONAL SURFACE

CROSS REFERENCE TO RELATED APPLICATIONS

The present application is a continuation in part of U.S. patent application Ser. No. 15/553,988, filed on Aug. 26, 2017, which is a National Stage Entry of PCT/US17/24871, filed Mar. 29, 2017, which are hereby incorporated by reference in their entirety.

BACKGROUND OF THE INVENTION

The present invention relates thermal packs.

The invention more particularly relates to thermal packs that are designed to conform to anatomical structures.

Thermal packs are applied to anatomical forms and other curved surfaces for transferring thermal energy by way of a thermal material, such as a water, gel or clay, in the pack. It is desirable for a thermal pack to conform as closely as possible to an anatomical form and other curved surfaces to which it is applied in order to achieve optimal energy transfer and comfort. Indeed, almost any thermal pack will conform closely to a flat surface or soft curve. However, anatomical forms such as the human body and other curved surfaces have bends and sharp curves as well.

While an improvement over a single-cell design, multi-cell thermal packs, as known in the art, may still not able to conform well to certain anatomical features or other curved surfaces, such as those that are generally round and/or have particularly sharp curves. This issue has been addressed to some extent by multi-cell thermal packs that are customized for specific anatomical features or other curved surfaces. However, such customized thermal packs may not conform well to other anatomical features or other curved surfaces.

It is known that the shape of a single-cell or multi-cell pack allows the pack to fit better on a curved surface. For example, a circular shaped pack may fit better on semi-spherical surface, such as a head. Whereas, a rectangle pack may fit better around an arm. However, shaping a single-cell or multi-cell pack to a curved surface has limitation. It may not be able to conform well to curved surfaces with multiple directional curves.

SUMMARY OF THE INVENTION

The present invention provides a method for creating a thermal-pack that approximates a three-dimensional surface including assessing a three-dimensional surface; flattening the accessed three-dimensional representation of the surface so as to produce a two-dimensional representation of the three-dimensional surface; forming a thermal pack that approximates the three-dimensional surface via the two-dimensional representation.

A three-dimensional surface, such as a shoulder may be assessed in a variety of ways including contact or non-contact 3D surface imaging. The result of the assessment is a fattened three-dimensional surface, i.e., a two-dimensional representation of the three-dimensional surface.

The two-dimensional representation is used to create a two dimensional thermal pack having the perimeter of the flattened three-dimensional surfaces. In some embodiments, a sack (die casting) is formed by joining a first and second sheet from a die in the form of a two-dimensional representation. The sack is filled with a thermal material and sealed.

The two-dimensional thermal pack is converted into a three-dimensional thermal pack by joining the appropriate adjacent edges of the perimeter of the two-dimensional thermal pack whereby seams are formed.

The present invention also provides for a thermal pack that approximates a three-dimensional surface comprising a first and second sheet joined to form a sack in the form of the flattened three-dimensional surface, the sack is filled with a thermal material and the thermal material is enclosed within the sack. The adjacent edges of the sack are joined at the seam lines such that the three-dimensional thermal pack approximates a three-dimensional surface.

The seams are oriented and shaped such that the three-dimensional thermal pack approximates a multidirectional-curved surface. The seams may curve such that the three-dimensional thermal pack approximates a curve with a variable radius. Whereas, one or more seams with intersecting directions will allow the pack to approximated.

The thermal pack may further comprise of mounts for attaching fasteners such that the thermal pack may be applied to a three-dimensional structure without having to be held on by hand.

The thermal pack may further comprise joint lines as described in patent application U.S. patent application Ser. No. 15/553,988 (national stage application of PCT/US17/24871) for the benefits described.

BRIEF DESCRIPTION OF THE DRAWINGS

In the accompanying figures, like elements are identified by like reference numerals among the several preferred embodiments of the present invention.

FIG. 1 is an example of a three-dimensional surface, namely a chin and jaw surface;

FIG. 2 is a simplified view of an embodiment of the invention illustrating first and second sheets of plastic that are joined together to form the thermal pack;

FIG. 3 is a top view of an embodiment of the invention illustrating a sack in the form of the flattened three-dimensional surface/two-dimensional representation before it is filled with thermal material;

FIG. 4 is a top view of an embodiment of the invention illustrating a sack in the form of the flattened three-dimensional surface/two-dimensional representation after the thermal material is enclosed in the sack;

FIG. 5 is a top view of an embodiment of the invention illustrating a sack in the form of the flattened three-dimensional surface/two-dimensional representation;

FIG. 6 is a side view of an embodiment of the invention formed by joining the first and second edges to form an approximation of the three-dimensional surface;

FIG. 7 is an example of a three-dimensional surface, namely a knee surface;

FIG. 8 is a simplified view of an embodiment of the invention illustrating first and second sheets of plastic that are joined together to form the thermal pack;

FIG. 9 is a top view of an embodiment of the invention illustrating a sack in the form of the flattened three-dimensional surface/two-dimensional representation illustrating a pattern of joint lines before it is filled with thermal material;

FIG. 10 is a top view of an embodiment of the invention illustrating a sack in the form of the flattened three-dimensional surface/two-dimensional representation illustrating a pattern of joint lines, after the thermal material is enclosed in the sack;

FIG. 11 is a top view of an embodiment of the invention illustrating a sack in the form of the flattened three-dimensional surface/two-dimensional representation illustrating a pattern of joint lines, showing the fastener system;

FIG. 12 is a side view of an embodiment of the invention formed by joining the first and second edges to form an approximation of the three-dimensional surface;

FIG. 14 is a model showing the distribution of gel according to the median; and

FIG. 15 is a model showing the distribution of gel according to the median.

DETAILED DESCRIPTION OF THE PREFERRED EMBODIMENTS

The foregoing and other features and advantages of the invention will become more apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Figure 2:
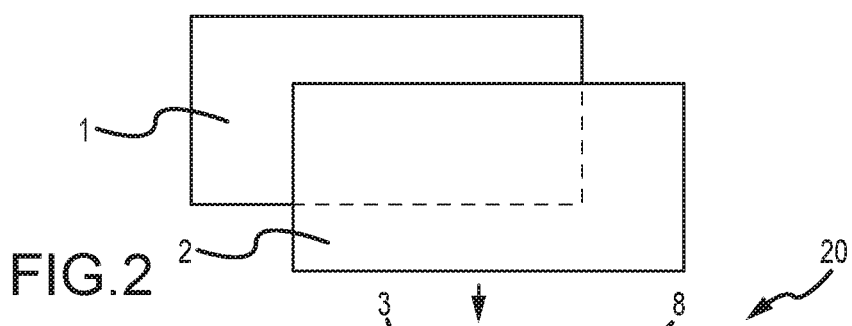
Figure 3:
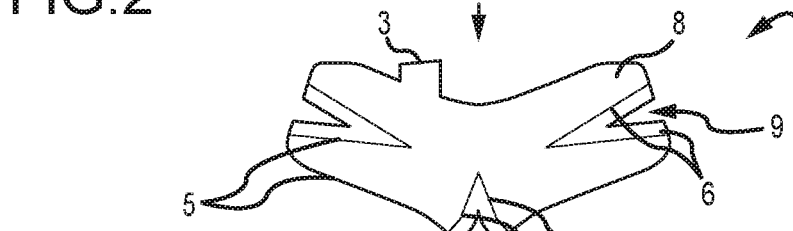
Figure 4:
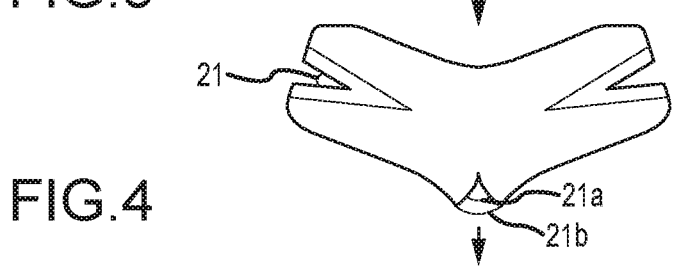
Figure 5:
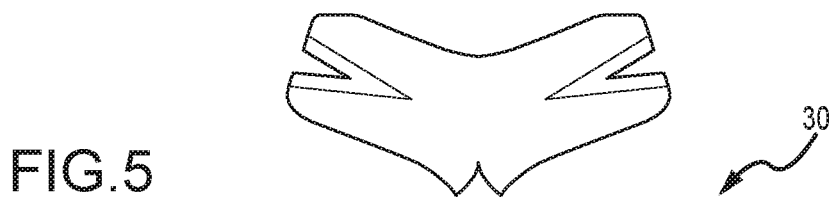
Figure 6:
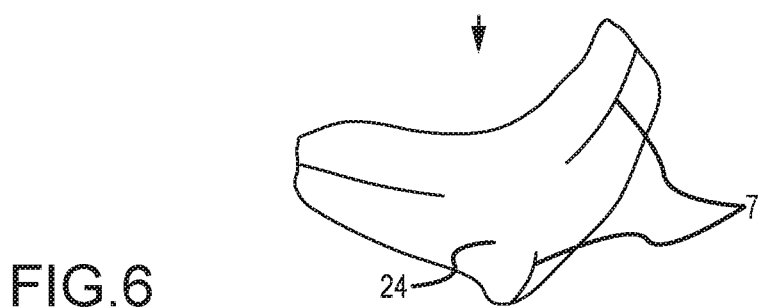
Figure 8:
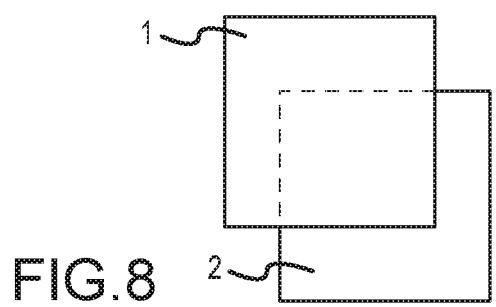
Figure 12:
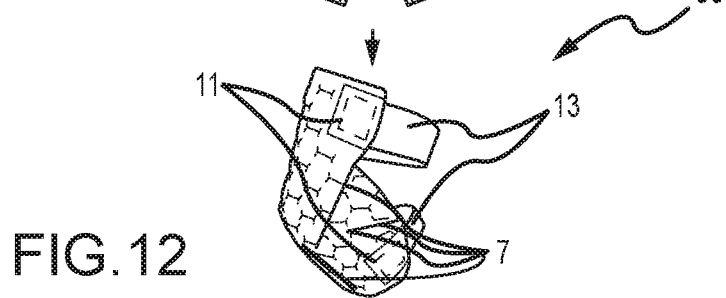
Figure 13:
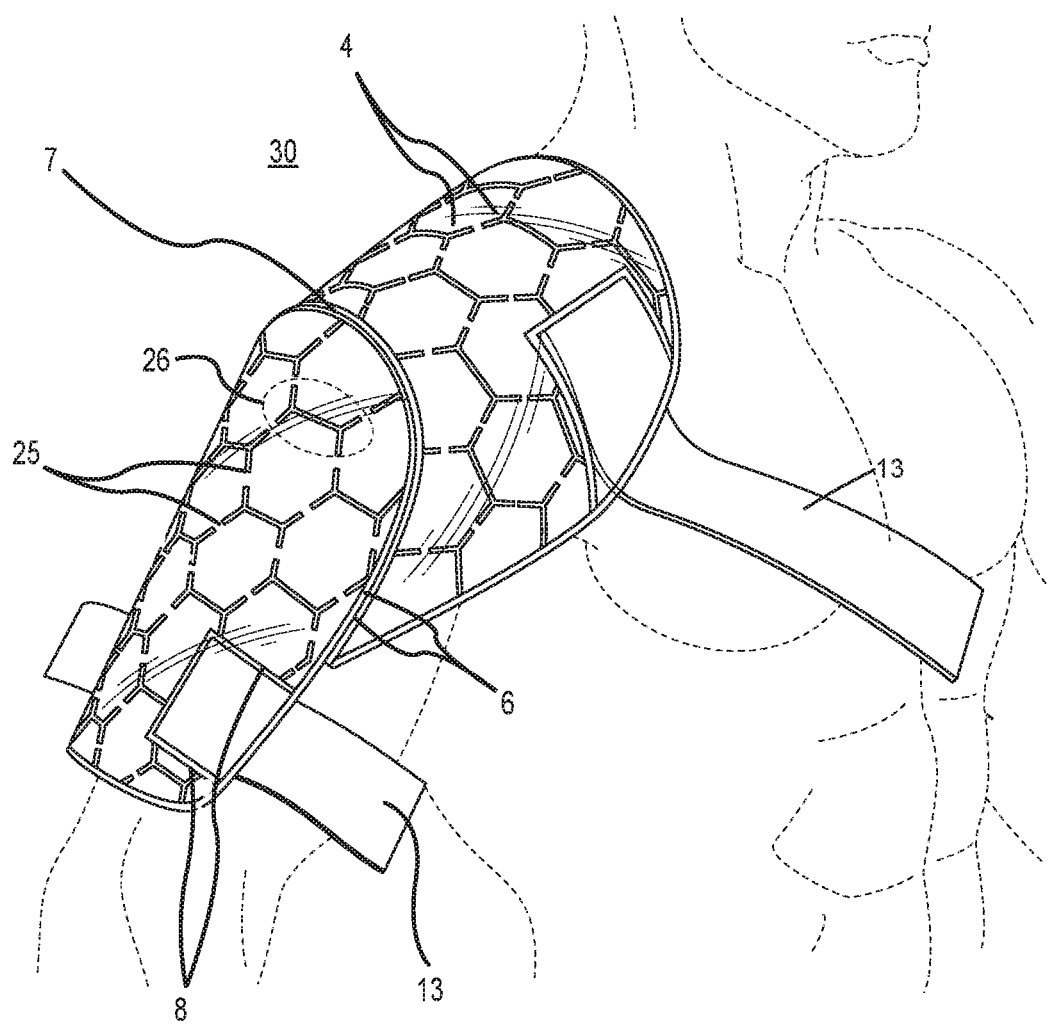
FIG. 13 is a perspective view of an embodiment of the invention that approximates a shoulder.

FIGS. 6, 12, and 13 depict a pack 30 in accordance with the invention for transferring heat to and from the body, comprising a sack 20 having a first and second sack edge 6 joined to form seams 7 and a body of thermal material 24 enclosed within the sack. In this particular embodiment, the pack 30 comprises a soft-plastic top sheet 1 and soft plastic bottom sheet 3 as shown in FIGS. 8 and 2. FIGS. 3-5 depict the two sheets 1 and 2 joined together at the perimeter of a two dimensional representation (not shown here) of a three-dimensional surface 10.

Figure 1:
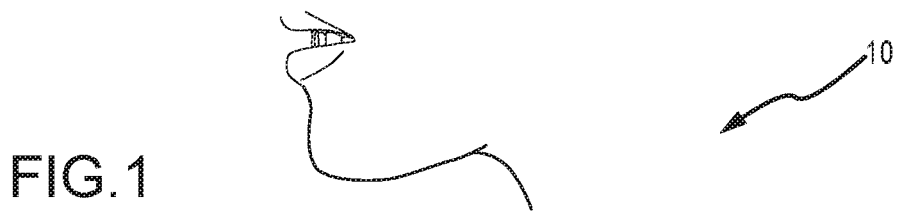
FIGS. 1-6 is a flow chart illustrating a method of making a thermal pack for a chin.
Figure 9:
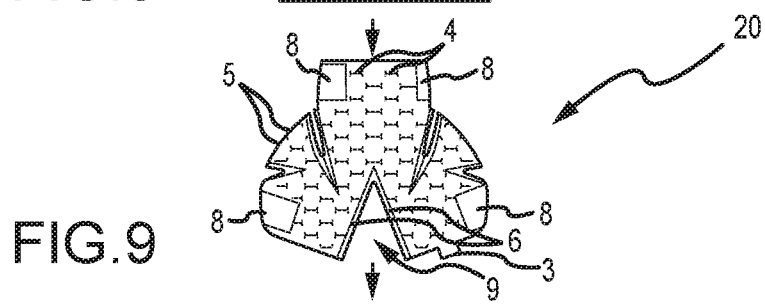
Figure 10:
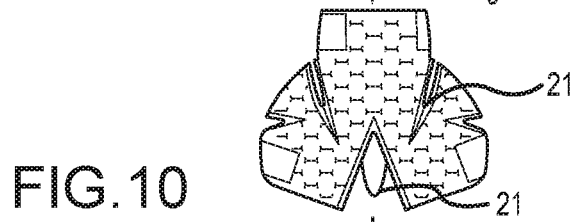
Figure 11:
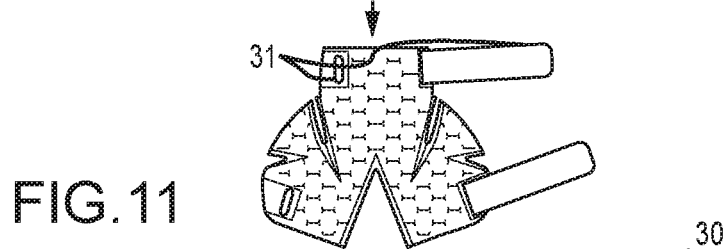

FIGS. 9-11, depict the two sheets 1 and 2 joined together at the perimeter of a two-dimensional representation (not shown here) of a three-dimensional surface 10 and at a plurality of joint lines 4. In these views only top sheet 2 is visible. As shown in FIG. 1., the three-dimensional surface is a chin and jaw. However, the three-dimensional surface does not need to be an anatomical feature, it could be any three-dimensional surface. FIGS. 4 and 10 show angle 21 between the intersecting directions of the first and second edges 6 that are joined to form a seam 7. The angle is less than 180 degrees such that when edges 6 are joined the pack 30 takes on a three-dimensional shape. The first and second edges 6 may be joined to form a seam 7 by heat sealing the edges together at the desired locations. As depicted in FIGS. 6 and 12 the resulting seam 7 allows the pack to conform to the three-dimensional surfaces shown in FIGS. 1 and 7 respectively. The three-dimensional surfaces 10 and respective packs 30 are merely illustrative. The seams 7 can be formed at desired locations to form the pack 30 into the desired three-dimensional shape.

The seams 7 may be formed at desired locations allow that pack to be in a plane substantially parallel to the approximated three-dimensional surface. In addition to allowing the pack to curve, the seams 7 may be configured to allow the pack 30 to lie flat. FIG. 12 illustrates the use of gathering seams 7. The pack 30 approximate the curve in the knee and the flat lateral and medial side of the knee. Where the three-dimensional structure is flat and curved, a gathering seam is formed where excess material is removed from the sack to allow it to approximate the three-dimensional surface and be in a place substantially parallel to the approximated three-dimensional surface.

As illustrated in FIG. 4, the first and second edges 6 may have intersecting directions with varying angles 21. For example, the intersecting directions of the first and second edge 6 form at least two angles 21a and 21b where angle 21a is smaller than angle 21b. The size of the angles 21 directly affects the curvature of the three-dimensional pack 30. The smaller the angle 21, the flatter the resulting curve. The larger the angle 21, the sharper the resulting curve. As illustrated in FIG. 6, angle 21a allows the pack to conform to the sharp curve of the chin running cheek to cheek. Whereas the larger angle 21b allows the pack 10 to conform to the curve running lip to neck. The first curve is flatter requiring a smaller angle 21 and the second curve is sharper requiring a larger angle 21. In assessing the three-dimensional surface 10, the relationship between the surface curves and angles 21 may be useful in flattening the three-dimensional surface 10.

Figure 7:
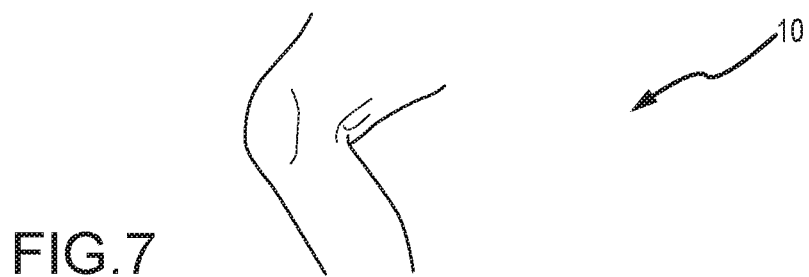
FIGS. 7-12 is a flow chart illustrating a method of making a thermal pack for a knee.

As illustrated in FIGS. 12 and 6, when the first and second edge 6 are joined to form seams 7, the curvature of the three-dimensional pack 30 is multidirectional. As shown in FIGS. 4 and 10, The varying angles 21 allow for multidirectional curvature in the pack 30 so that it approximates the three-dimensional surface 10. FIGS. 1 and 7 as depicted illustrate surfaces having a multidirectional curved surface. FIG. 1 illustrates a curve over the chin, cheek to cheek and a second curve over the chin, throat to lip. FIG. 6 illustrates how seam 7 is configured such that the pack 30 conforms to the multidirectional curved surface shown in FIG. 1. In another example, FIG. 7 illustrates a curve across the thigh from the lateral side to the medial side, a curve across the knee from proximal to distal portions of the knee and a curve across the shin from the lateral side to the medial side. FIG. 12 illustrates how the seams 7 are configured differently such that the pack 30 approximates a different three-dimensional surface.

As illustrated in FIGS. 14 and 15, the sacks may have a median thickness of approximately 50% whereby 50% of the thermal material is above the mid plane 27 and 50% is below the mid plane 27.

In a particular embodiment, the thermal material 24 enclosed in the pack 30 is a bentonite and glycol blend which can be heated above body temperature for transferring heat to the body and chilled for absorbing heat from the body. This mixture will not freeze solid when cooled at normal freezer temperatures of approximately zero degrees Fahrenheit. A pack 30 with this type of thermal material 24 further allows the pack 30 to conform to the body. In a particular embodiment, the thermal material has a heat capacity greater than 0.4. In a particular embodiment, the thermal material has a higher viscosity than water. In a particular embodiment, the thermal material, has a higher viscosity than 50,000 centipoise. In a particular embodiment, the thermal material has a viscosity higher than 150,000 centipoise.

The presence of the joint lines 4 inhibit the thermal material 24 within the pack from flowing so freely within the pack as to result in the thermal material 24 pooling at the pack 10 edges under pressure caused by the flexing and/or under the influence of gravity, as would tend to be the case of a pack 30 with flowable thermal material 24 that does not have joint lines 4, e.g. a singlecell pack. As such, it may be advantageous for the joint lines 4 and gaps 25 to be arranged in such a way as to minimize or eliminate straight-line paths for the flow of thermal material 7 through the gaps 25. As depicted in FIG. 13, for example, a pack 30 meeting this criterion has joint lines 4 arranged to form a pattern of tessellated hexagons with gaps 25 and joint lines 4 constituting the hexagon edges. A pattern may be formed by any desired cell shapes and/or arrangement of joint shapes 26 and/or joint lines 4.

In practice, the pack 30 may be of any suitable material and, in particular embodiments the sheets are of plastic. One possibility is a polymer, such as polyethylene, polyester, polypropylene, nylon, poly-vinyl chloride, and combinations of these materials, as well as laminates of multiple materials. The pack 30 may be free of latex and other allergenic materials. The pack 30 may also be textured on its exterior for comfortable contact with skin of the body. As depicted in FIGS. 12 and 13, an embodiment of the pack 30 comprises one or more straps 13 mounted to the pack 30 at a strap mount 8. However, the thermal pack 30 may be secured to an anatomical structure in a variety of ways with or without any of a variety of fasteners. For example, a person may hold the thermal pack against a portion of the body. The present inventor has found the thermal pack 30 is advantageously secured to the body with straps 13 mounted to the pack having a hook and loop system 14, as shown in FIG. 7. The straps 13 are mounted to the pack 10 by being fastened to or through one or more apertures 15 formed in the pack 10 and fastened back on itself with a hook and loop system 31.

A particular method of making a pack 30 that approximates the surface of a selected area of a three-dimensional surface 10. The portion of a three-dimensional surface 10 approximated here is a chin and jaw. In this particular-version of the claimed method, the three-dimensional surface 10 is accessed. The three-dimensional surface may be accessed by many known methods including but not limited contact or non-contact surface imaging. For example, a contact method of surface imaging may include creating a three-dimensional physical mold of the three-dimensional surface 10. A non-contact method may include using software to create an image of the surface 10. The accessed three-dimensional surface 10 is flattened into a two-dimensional representation (not shown) of the three-dimensional surface 10. The surface may be flattened by physically flattening a mold of the three-dimensional representation. Another method may be to use software for flattening a three-dimensional surface.

The two-dimensional representation is used to create one or more molds. A first pliable plastic sheet 1 and second pliable plastic sheet 2 are joined to form a sack 20 in the form of the two-dimensional representation. The first and second sheet are joined at the borders of the flattened three-dimensional surface 10. The sack 20 contains a fill opening 3 such that the sack 20 may be filled with a thermal material. The thermal material (not shown) is enclosed in the sack 20 by sealing the fill opening 3. The fill opening 3 may be heat sealed to enclose the thermal material 24 within the sack 20. The sack edges 6 are joined to form seams 7 whereby the sack 20 approximates the three-dimensional surface. This invention is not limited to forming a thermal pack out of one sack 20. The thermal pack may be made by joining multiple sacks 20 such that the final structure approximates the three-dimensional surface 10.

A particular method of making a thermal pack includes using the technique of die casting. The two-dimensional representation is used to create a mold wherein the first sheet 1 and the second sheet 2 are die cut into the two-dimensional representation (not shown). The first sheet 1 and the second sheet 2 of plastic having a thickness between 0.05 millimeters and 0.5 millimeters. The mold may be formed to have additional features beyond the perimeter of the flattened three-dimensional surface. The mold may include, for example a structure to create an opening 3 in the sack 20 for filing the sack 20 with the thermal material (not shown), jointed lines 4 as shown in FIG. 2 and further described in U.S. patent application Ser. No. 15/553,988 (national stage application of PCT/US17/24871) or mounts 8 and fastener openings 12 for attaching any type of fastener 13 including but not limited to a loop-through fastener with a hook and loop system. As shown in FIG. 2, the fastener 13 is not limited to a loop-through fastener with a hook and loop system. The fastener may comprise a mounted elastic straps 13 attached at mounts 8.

The foregoing merely illustrates the principles of the invention. It will be appreciated that those skilled in the art will be able to devise numerous alternative arrangements that while not shown or described herein, embody the principles of the invention and thus are within its spirit and scope.

The invention claimed is:

1. A method of making a thermal pack, which comprises
a. assessing a three-dimensional surface;
b. flattening the assessed three-dimensional surface into a two-dimensional representation of the three-dimensional surface;
c. forming a first pliable sheet and second pliable sheet into the form of the two-dimensional representation;
d. forming one or more sacks by aligning and joining the first pliable sheet with and to the second pliable sheet;
e. forming a plurality of elongated joint lines joining internal portions of the one or more sacks within the thermal pack, the plurality of elongated joint lines forming a tessellated plurality of hexagonal shaped thermal material cells;

the hexagonal shaped thermal material cells having six faces wherein a first face joins a second face forming a first obtuse angle section, the second face joins a third face forming a second obtuse angled section, the third face joins a fourth face forming a third obtuse angled section, the fourth face joins a fifth face forming a fourth obtuse angled section, the fifth face joins the a sixth face forming a fifth obtuse angled section, the sixth face joins the first face forming a sixth obtuse angled section;

the hexagonal shaped thermal material cells further having a first gap disposed in the first face, a second gap is disposed in the second face, a third gap is disposed in the fourth face, and a fourth gap is disposed in the fifth face;

the hexagonal shaped thermal cells having an upper thermal material retaining portion comprising the first obtuse angled section, the second face, and the second obtuse angled section configured to deflect thermal material flow towards a thermal cell center;

the hexagonal shaped thermal material cells further having a first lateral thermal material retaining portion comprising the sixth obtuse angled section and a second lateral thermal material retaining portion comprising the third obtuse angled section, the first and second lateral thermal material retaining portions configured to deflect thermal material flow towards the thermal cell center; and the hexagonal shaped thermal cells having an lower thermal material retaining portion comprising the fourth obtuse angled section, the fifth face, and the fifth obtuse angled section configured to retain thermal material flowing into the hexagonal shaped thermal cells and deflect excess thermal material flow towards the thermal cell center;

f. filling the one or more sacks with the thermal material; and g. enclosing the thermal material within the one or more sacks.

2. A method of making a thermal pack of claim 1, wherein the step of assessing a three-dimensional surface comprises assessing the three-dimensional surface with three dimensional surface imaging wherein a virtual three-dimensional surface is created and the step of flattening the assessed three-dimensional surface comprises virtually flattening the virtual three-dimensional surface and projecting the flattened virtual three-dimensional surface as the two-dimensional representation.

3. A method of making a thermal pack of claim 1 wherein the one or more sacks comprises two or more sacks and the two or more sacks are permanently bonded together along a perimeter curve of each sack of two or more sacks forming a seam following a three-dimensional trajectory such that the bonded two or more sacks form a sack interior surface shaped as the three-dimensional surface wherein all thermal material cells align substantially parallel to the three-dimensional surface.

4. A method of making a thermal pack of claim 1 which further comprises joining a fastener system to the thermal pack.

5. A method of making a thermal pack of claim 1 forming an opening in the one or more sacks for filling the one or more sacks with the thermal material.

6. A method of making a thermal pack of claim 1, wherein the three-dimensional surface is assessed by creating a three-dimensional physical mold of the three-dimensional surface and the three-dimensional physical mold is then flattened.

7. A method of making a thermal pack of claim 1, wherein the step of forming a first pliable sheet and second pliable sheet into the form of the two-dimensional representation further includes forming at least one relief cut into the two-dimensional representation, the at least one relief cut having a first edge and a second edge and an angle between the first edge and second edge measuring between 0 degrees and 180 degrees.

8. A method of making a thermal pack of claim 7, further including the steps of joining the first edge and the second edge of the at least one relief cut forming a seam approximating a multidirectional-curved surface thus causing the one or more sacks to flex into and form the three-dimensional surface.

9. A method of making a thermal pack of claim 8, wherein the seam approximates a multidirectional curve having a variable radius.

10. A method of making a thermal pack of claim 7, wherein the one or more sacks comprise an interior three-dimensional surface mating area, and wherein a seam is formed to allow each portion of the interior three-dimensional surface mating area to be in a plane substantially parallel to the three-dimensional surface.

11. A method of making a thermal pack, which comprises
(a) assessing a three-dimensional surface;
(b) flattening the assessed three-dimensional surface into a two-dimensional representation of the assessed three-dimensional surface;
(c) forming one or more dies in the form of the two-dimensional representation;

(d) die cutting the two-dimensional representation from a first pliable sheet and second pliable sheet and forming one or more sacks;

(e) forming a plurality of elongated joint lines joining internal portions of the one or more sacks within the thermal pack, the plurality of elongated joint lines forming a tessellated plurality of hexagonal shaped thermal material cells;

the hexagonal shaped thermal material cells having six faces wherein a first face joins a second face forming a first obtuse angle section, the second face joins a third face forming a second obtuse angled section, the third face joins a fourth face forming a third obtuse angled section, the fourth face joins a fifth face forming a fourth obtuse angled section, the fifth face joins the a sixth face forming a fifth obtuse angled section, the sixth face joins the first face forming a sixth obtuse angled section;

the hexagonal shaped thermal material cells further having a first gap disposed in the first face, a second gap is disposed in the second face, a third gap is disposed in the fourth face, and a fourth gap is disposed in the fifth face;

the hexagonal shaped thermal cells having an upper thermal material retaining portion comprising the first obtuse angled section, the second face, and the second obtuse angled section configured to deflect thermal material flow towards a thermal cell center;

the hexagonal shaped thermal material cells further having a first lateral thermal material retaining portion comprising the sixth obtuse angled section and a second lateral thermal material retaining portion comprising the third obtuse angled section, the first and second lateral thermal material retaining portions configured to deflect thermal material flow towards the thermal cell center; and the hexagonal shaped thermal cells having an lower thermal material retaining portion comprising the fourth obtuse angled section, the fifth face, and the fifth obtuse angled section configured to retain thermal material flowing into the hexagonal shaped thermal cells and deflect excess thermal material flow towards the thermal cell center;

(f) filling the one or more sacks with the thermal material; and (g) enclosing the thermal material within the one or more sacks.

12. A method of making a thermal pack of claim 11, wherein the step of assessing a three-dimensional surface comprises assessing the three-dimensional surface with three dimensional surface imaging wherein a virtual three-dimensional surface is created and the step of flattening the assessed three-dimensional surface comprises virtually flattening the virtual three-dimensional surface and projecting the virtual three-dimensional surface as the two-dimensional representation.

13. A method of making a thermal pack of claim 11 wherein enclosing the thermal material within the one or more sacks further comprises joining the first and second sheet at an opening.

14. A method of making a thermal pack of claim 11 which further comprises joining a fastener system to the thermal pack.

15. A method of making a thermal pack of claim 11, wherein the three-dimensional surface is assessed by creating a three-dimensional physical mold of the three-dimensional surface and the three-dimensional physical mold is then flattened.

16. A method of making a thermal pack of claim 11, wherein the step of flattening the assessed three-dimensional surface into a two-dimensional representation of the assessed three-dimensional surface further includes forming at least one relief cut into the two-dimensional representation, the at least one relief cut having a first edge and a second edge and an angle between the first edge and second edge measuring between 0 degrees and 180 degrees.

17. A method of making a thermal pack of claim 16, further including the steps of joining the first edge and the second edge of the at least one relief cut forming a seam approximating a multidirectional-curved surface thus causing the one or more sacks to flex into and form the three-dimensional surface.

18. A method of making a thermal pack of claim 16, wherein the seam approximates a multidirectional curve having a variable radius.

19. A method of making a thermal pack of claim 17, wherein the one or more sacks comprise an interior three-dimensional surface mating area, and wherein the seam is formed to allow each portion of the interior three-dimensional surface mating area to be in a plane substantially parallel to the three-dimensional surface.

20. A method of making a thermal pack of claim 11 wherein the one or more sacks comprises two or more sacks and the two or more sacks are permanently bonded together along a perimeter curve of each sack of the two or more sacks forming a seam following a three-dimensional trajectory such that the bonded two or more sacks form a sack interior surface shaped as the three-dimensional surface wherein all thermal material cells align substantially parallel to the three-dimensional surface.

* * * * *